United States Patent [19]

Matsumoto et al.

[11] Patent Number: 5,625,102
[45] Date of Patent: Apr. 29, 1997

[54] METHOD OF ALKYLATING THE SIDE CHAIN OF ALKYL-SUBSTITUTED AROMATIC HYDROCARBONS

[75] Inventors: Takaya Matsumoto; Yoshiichi Kumagai; Fumio Kumata, all of Kanagawa, Japan

[73] Assignee: Mitsubishi Oil Co., Ltd., Tokyo, Japan

[21] Appl. No.: 364,446

[22] Filed: Dec. 27, 1994

[30] Foreign Application Priority Data

Dec. 27, 1993 [JP] Japan ................... 5-346937

[51] Int. Cl.$^6$ ............... C07C 15/067; C07C 2/72
[52] U.S. Cl. ............... 585/453; 585/410; 585/411; 585/446; 585/452; 585/455; 585/467; 502/340; 502/341; 502/344; 502/355
[58] Field of Search ............... 585/410, 411, 585/446, 452, 455, 467, 453; 502/340, 341, 344, 355

[56] References Cited

U.S. PATENT DOCUMENTS

| | | | |
|---|---|---|---|
| 4,034,052 | 7/1977 | Puskas | 585/438 |
| 4,962,254 | 10/1990 | Fukao et al. | 585/452 |
| 5,097,088 | 3/1992 | Fukao et al. | 585/453 |
| 5,118,895 | 6/1992 | Hibi et al. | 585/452 |
| 5,227,559 | 7/1993 | Fukao et al. | 585/452 |
| 5,347,062 | 9/1994 | Fukao et al. | 585/452 |

FOREIGN PATENT DOCUMENTS

| | | | |
|---|---|---|---|
| 0128001 | 12/1984 | European Pat. Off. . | |
| 0328940 | 8/1989 | European Pat. Off. . | |
| 221133 | 10/1986 | Japan | C07C 2/72 |
| 62-209027 | 9/1987 | Japan | C07C 2/72 |
| 2-138229 | 5/1990 | Japan | C07C 15/02 |
| 2-178236 | 7/1990 | Japan | C07C 15/00 |
| 3-227944 | 10/1991 | Japan | C07C 15/00 |
| 3-264539 | 11/1991 | Japan | C07C 15/00 |
| WO9014323 | 11/1990 | WIPO . | |

*Primary Examiner*—Glenn A. Caldarola
*Assistant Examiner*—Elizabeth D. Woop
*Attorney, Agent, or Firm*—Sughrue, Mion, Zinn, Macpeak & Seas

[57] ABSTRACT

A method of alkylating the side chain of alkyl-substituted aromatic hydrocarbons. The method comprises the steps of thermally treating an alumina by calcining in air and then degassing under vacuum to prepare an alumina carrier, loading an alkali metal on the alumina carrier by an impregnation method using the alkali metal dissolved in liquid ammonia, thermally treating the alkali metal loaded alumina carrier under vacuum to prepare a catalyst, then reacting an alkyl-substituted aromatic hydrocarbon with an aliphatic monoolefin, using the catalyst, under an atmosphere substantially free of oxygen, water and carbon dioxide gas to alkylate the side chain of the alkyl-substituted aromatic hydrocarbon.

12 Claims, No Drawings

METHOD OF ALKYLATING THE SIDE CHAIN OF ALKYL-SUBSTITUTED AROMATIC HYDROCARBONS

FIELD OF THE INVENTION

The present invention relates to a method of alkylating the side chain of alkyl-substituted aromatic hydrocarbons. More specifically, the present invention relates, for instance, to the economical production of 2-methyl-1-(p-tolyl)-butane by alkylation of the side chains of p-xylene with butene. By conducting a cyclic dehydration, the 2-methyl-1-(p-tolyl) butane can form 2,6-dimethylnaphthalene, which is an industrially useful, polymerizable raw material. Thus, the present invention relates to an economical synthesis method for industrially useful, alkyl-substituted aromatic hydrocarbons.

BACKGROUND OF THE INVENTION

The alkylating reaction for the side chain of alkyl-substituted aromatic hydrocarbons by aliphatic monoolefins is conventionally well known (e.g., H. Pines 5, *J. Am. Chem. Soc.*, vol. 77 (1955)). However, this method is disadvantageous in that used sodium cannot be recovered, and a large amount thereof is necessary since metallic sodium is directly added to the reaction solution and is used in a suspended state.

To avoid this disadvantage, a variety of methods have been proposed to load an alkali metal on a carrier for solidification. For example, U.K. Patent 1,269,280 and JP-A-61-221133 propose the use of a potassium carbonate loaded sodium, JP-A-62-209027 proposes the use of a potassium phosphate loaded sodium, JP-A-2-138229 (corresponding to U.S. Pat. No. 5,347,062) proposes the use of a potassium hydroxide-alumina loaded potassium, JP-A-2-178236 (corresponding to U.S. Pat. No. 5,227,559) proposes the use of an alumina loaded potassium, JP-A-3-264539 (U.S. Pat. No. 5,118,895) proposes the use of a magnesia loaded potassium, JP-A-3-227944 (U.S. Pat. No. 5,097,088) proposes the use of a magnesia-alumina loaded potassium, etc. (The term "JP-A"as used herein means "unexamined published Japanese patent application".) In these proposals, the use of aliphatic monoolefins such as ethylene, propylene and butene is examined, and the reactivity decreases in the order of ethylene>propylene>butene, thus the reactivity of butene is lowest.

With respect to a conventional catalyst, a catalyst in which an alkali metal is loaded on a basic, carrier has a high activity, but it is disadvantageous in that the basic carrier has such a small specific area that the alkali metal loaded thereon is not sufficiently dispersed. On the other hand, an alumina catalyst in which an alkali metal is loaded on alumina has a large specific area and shows a good dispersibility for the loaded metal. However, because of the acidic nature of alumina, the alumina catalyst cannot provide a sufficient activity for alkylating the side chain, by conventional catalyst production methods.

SUMMARY OF THE INVENTION

An object of the present invention is to provide a novel method of alkylating the side chain of alkyl-substituted aromatic hydrocarbons by aliphatic monoolefins. In particular, the present invention relates to a novel method which efficiently synthesizes 2-methyl-1-(p-tolyl)-butane by causing the side chain alkylation of p-xylene, at a high conversion rate, using low reactive butene as a raw material.

The reaction system of the present invention potentially entails some side reactions such as formation of a butene dimer by reaction between butenes and alkylation of benzene ring by reaction between p-xylene and butene, etc.

Another object of the present invention is to minimize as much as possible, such side reactions from occurring. In order to inhibit dimerization of butene, it is effective, for instance, to lower the reaction temperature and the reactant concentration, which also requires to develop a catalyst having a sufficient activity at a low temperature or a low concentration. In order to inhibit alkylation of benzene ring, it is required to decrease the acidity of a catalyst carrier, which is accomplished by loading an alkali amide.

As a result of an intensive study for a method of reacting aliphatic monoolefins, especially low reactive butene, the present inventors have found that 2-methyl-1-(p-tolyl) butane can be formed with a high conversion rate and a high selectivity rate by a method comprising the use of a catalyst in which an alkali metal dissolved in liquid ammonia is loaded on an alumina having a large specific area as a carrier, by an impregnation method, and then conducting a reaction in an atmosphere substantially free from oxygen, water and carbon dioxide gas.

More specifically, the present invention is accomplished by a method of alkylating the side chain of alkyl-substituted aromatic hydrocarbons, which comprises thermally treating an alumina by previously calcining in air and then degassing under vacuum to prepare an alumina carrier, loading an alkali metal on the alumina carrier by an impregnation method using the alkali metal dissolved in liquid ammonia, thermally treating the alkali metal loaded alumina carrier under vacuum to prepare a catalyst, then reacting an alkyl-substituted aromatic hydrocarbon with an aliphatic monoolefin using the catalyst under an atmosphere substantially free of oxygen, water and carbon dioxide gas to alkylate the side chain of the alkyl-substituted aromatic hydrocarbon.

DETAILED DESCRIPTION OF THE INVENTION

Alkyl-substituted aromatic hydrocarbons such as toluene, xylene, ethylbenzene, trimethylbenzene, methylnaphthalene and the like bring about a similar side chain alkylation reaction. In the case of producing 2-methyl-1-(p-tolyl)-butane, which is useful as a polymerizable raw material, p-xylene is preferably used as a reactant. In this case, as a raw p-xylene material, it is desirable to have impurities in as small an amount as possible, and it is preferable to have a purity of 99.5% or more. One of the impurities present therein is ethylbenzene whose boiling point is nearly close to that of p-xylene. In addition thereto, impurities therein include a small amount of water, oxygen and carbon dioxide gas. Since this small amount of impurities adversely affects the catalyst, it is preferable to limit the water content to 1 ppm or less, the oxygen content to 10 ppm or less, and the carbon dioxide content to 1 ppm or less.

Aliphatic monoolefins such as ethylene, propylene, butene, heptene and the like bring about a similar reaction. In the case of producing 2-methyl-1-(p-tolyl)-butane, butene is preferably used. Though the butene includes 1-butene or 2butene, each butene can be used since each one provides the same reaction. This is because when a catalyst of the present invention is used, the isomerization of butene proceeds very rapidly, reaching the equilibrium composition quickly. As a raw material for butene, it is typical to use a product obtained by the heat decomposition or the catalytic cracking of petroleum, though it is not essential, and any butene produced by any process can be used. However, it is preferable to limit the water content to 1 ppm or less, the oxygen content to 10 ppm or less, and the carbon dioxide content to 1 ppm or less, as well as in the case of p-xylene.

A catalyst for use in the present invention can be prepared as follows:

As a carrier, it is possible to use various types of alumina having a different crystalline structure such as γ-alumina, η-alumina and α-alumina. The use of γ-alumina is common, since it has a comparatively large specific area and is stable. Before the use, alumina is thermally treated to remove the impurities on the surface thereof. When thermally treated, alumina is first calcined in air, then degassed under vacuum. The thermal treatment for calcination and degassing is conducted each at 100° to 1,000° C., preferably at 400° to 700° C. for 1 to 20 hours, preferably 2 to 10 hours.

After degassing under vacuum, the alumina is cooled, then an alkali metal is added thereto in an inert gas atmosphere by introducing an inert gas such as helium gas and nitrogen gas. The amount of alkali metal added is 0.5 to 40 wt %, preferably 2 to 30 wt %, based on the amount of the alumina carrier. After addition of the alkali metal, the resulting product is cooled to −33° C. (which is the boiling point of ammonia) or lower, under reduced pressure. When ammonia gas is introduced thereto, the ammonia becomes liquid, i.e., liquid ammonia. An alkali metal is easily soluble in liquid ammonia. After dissolving, the system is allowed to stand for a while in order to reach room temperature, and then ammonia gas is exhausted therefrom. As alkali metals, sodium or potassium, is preferred.

After exhausting ammonia gas, the system is further thermally treated under vacuum. The thermal treatment is conducted at 100° to 500° C., preferably at 200° to 400° C. for 10 minutes to 10 hours, preferably at 1 to 5 hours.

The catalyst thus prepared is used to effect reaction. The reaction can be conducted by either a batch process or a continuous process. In a laboratory, it is convenient to use a batch process. Industrially, it is preferred to use a continuous process.

In a batch process, the catalyst thus prepared is placed in a reactor, in an inert gas atmosphere, then the reactor is charged with a purified alkyl-substituted aromatic hydrocarbon. After the system is elevated to the reaction temperature, an aliphatic monoolefin is added thereto.

In a batch process, the amount of catalyst is in the range of 0.1 to 20 wt %, preferably 2 to 10 wt %, based on the amount of alkyl-substituted aromatic hydrocarbon. However, the amount of catalyst may vary depending on the alkali metal loading amount, the reaction temperature, and the reaction period. Generally, from the thermodynamic equilibrium standpoint, it is advantageous to apply a lower reaction temperature, but from the reaction speed standpoint, it is advantageous to apply a higher temperature. Usually, the reaction is conducted at 100° to 400° C., preferably at 150° to 300° C. for 1 to 20 hours, preferably 2 to 10 hours. Also, from the thermodynamic equilibrium standpoint, it is advantageous to apply a higher pressure, but a pressurized energy is required for a higher pressure and necessitates an expensive device. Usually, the reaction is conducted under 5 to 100 kg/cm², preferably at 20 to 80 kg/cm².

Examples of a continuous process include, for example, a fixed bed flow type reactor, a fluidized bed type reactor, a continuous batch type reactor, etc. In addition, examples thereof include various types of reactors, such as a fixed bed type reaction distillation type reactor and a boiling bed type reactor. Any of these reactors are useful. The reaction conditions in the continuous type process are similar to those in the batch type process, since the reaction involved does not change.

The present invention will now be illustrated in greater detail with reference to the following Examples, but the present invention should not be construed as being limited thereto. Unless otherwise indicated herein, all parts, percents, ratios and the like are by weight.

EXAMPLE 1

(1) Preparation of Catalyst.

5 g of γ-alumina powder having a specific area of 320 m²/g was calcined at 550° C. for 3 hours in air. After calcining, the resulting product was degassed under vacuum, then maintained under vacuum for 3 hours. After degassing, an inert nitrogen gas was introduced thereto. Then, the system was allowed to reach normal pressure, and the temperature was decreased. After reaching room temperature, 1.0 g of metallic sodium was added thereto while passing nitrogen gas through the system. The mixture of metallic sodium and γ-alumina was cooled to −33° C. or lower with dry ice and a methanol solution, then degassed under vacuum. Ammonia gas was then added to liquify the ammonia for dissolving the metallic sodium in liquid ammonia. After the system was allowed to stand for 1 hour, it was gradually elevated to room temperature. The vaporized ammonia generated was removed by evacuation. Further, the system was elevated to 300° C. and the system was maintained for 3 hours. Thereafter, the system was cooled to room temperature and stored in nitrogen gas. The catalyst thus obtained was designated as Catalyst A.

(2) Synthesis Reaction of 2-Methyl-1-(p-Tolyl)-Butane 50 ml of purified p-xylene having a purity of 99.8% and 5 g of Catalyst A were added to a reactor having an inner volume of 150 ml. After being covered with a nitrogen atmosphere, the system was elevated to 180° C. After reaching 180° C., 9.8 g of butene was poured into the mixture, and the reaction was conducted for 3 hours.

EXAMPLE 2

Catalyst B was prepared in the same manner as in Example 1, except that 1.0 g of metallic potassium was added instead of 1.0 g of metallic sodium. Then the reaction was conducted in the same manner as in Example 1, except for the use of Catalyst B instead of Catalyst A.

EXAMPLE 3

Catalyst C was prepared in the same manner as in Example 1, except that 0.25 g of metallic sodium was used. Then, the reaction was conducted in the same manner as in Example 1, except for the use of Catalyst C instead of Catalyst A.

EXAMPLE 4

Catalyst D was prepared in the same manner as in Example 1, except that 0.25 g of metallic potassium was used instead of 1.0 g of metallic sodium. Then, the reaction was conducted in the same manner as in Example 1, except that Catalyst D was used instead of Catalyst A, the reaction temperature was changed to 220° C., and the reaction time was changed to 5 hours.

COMPARATIVE EXAMPLE 1

Catalyst E was prepared in the same manner as in Example 1, except that the temperature elevation was not conducted after the ammonia evacuation. Then, the reaction was conducted in the same manner as in Example 1, except for the use of Catalyst E instead of Catalyst A.

The results obtained are shown in Table 1 below.

TABLE 1

Results of Synthesis Reaction of
2-Methyl-1-(p-Tolyl)-Butene (2MTB)

| | Catalyst | p-Xylene Conversion (%) | Butene Conversion (%) | 2MTB Yield (%) | 2MTB Selectivity (%) |
|---|---|---|---|---|---|
| Example 1 | A | 22 | 61 | 15 | 68 |
| Example 2 | B | 18 | 58 | 13 | 72 |
| Example 3 | C | 35 | 88 | 24 | 69 |
| Example 4 | D | 41 | 95 | 29 | 71 |
| Com. Ex. 1 | E | 0.5 | 0.7 | 0.3 | 60 |

Note:
2MTB Selectivity = (2MTB Yield/p-Xylene Conversion) × 100

From the results in Table 1 above, it is apparent that a catalyst which was prepared by not conducting a temperature elevation after the evacuation (Catalyst E) was remarkably inferior in activity as compared to the catalysts of the present invention.

As described above, the present invention makes it possible to alkylate the side chains of p-xylene using butene, with a high conversion rate, which has been conventionally considered to be difficult. Moreover, the present invention also makes it possible to obtain 2-methyl-1-(p-tolyl)-butane with a high selectivity rate. Previous methods utilized to obtain this compound have been quite expensive. By the cyclical dehydration of the compound using conventional techniques, the present invention makes it possible to economically produce 2,6-dimethylnaphthalene as raw material for a useful high molecular weight material.

While the invention has been described in detail and with reference to specific examples thereof, it will be apparent to one of ordinary skill in the art that various changes and modifications can be made herein without departing from the spirit and scope of the invention.

What is claimed is:

1. A method of alkylating the side chain of an alkyl-substituted aromatic hydrocarbon, comprising the steps of:

(A) thermally treating an alumina by calcining in air at 100° to 1000° C. for 1 to 20 hours and degassing under vacuum so as to prepare a thermally treated alumina carrier;

(B) loading an alkali metal on the thermally treated alumina carrier of step (A) by an impregnation method, wherein the alkali metal is contacted with the thermally treated alumina carrier while the alkali metal is dissolved in liquid ammonia, so as to prepare an alkali metal loaded alumina carrier;

(C) thermally treating the alkali metal loaded alumina carrier of step (B) at 100° to 500° C. for 10 minutes to 10 hours under vacuum, so as to prepare a catalyst; and (D) reacting an alkyl-substituted aromatic hydrocarbon with an aliphatic monoolefin using the catalyst of step (C) under an atmosphere substantially free of oxygen, water and carbon dioxide gas to alkylate a side chain of the alkyl-substituted aromatic hydrocarbon.

2. The method of claim 1, wherein the alkyl-substituted aromatic hydrocarbon is p-xylene.

3. The method of claim 1, wherein the aliphatic monoolefin is butene.

4. The method of claim 2, wherein the aliphatic monoolefin is butene.

5. The method of claim 1, wherein the alkali metal is potassium or sodium.

6. The method of claim 1, wherein the alumina is γ-alumina.

7. The method of claim 1, wherein the thermal treatment in step (A) is conducted at 400° to 700° C. for 2 to 10 hours.

8. The method of claim 1, wherein the alkali metal is loaded in step (B) in an amount of 0.5 to 40% by weight based on the amount of the thermally treated alumina carrier of step (A).

9. The method of claim 8, wherein the alkali metal is loaded in step (B) in an amount of 2 to 30% by weight based on the amount of the thermally treated alumina carrier of step (A).

10. The method of claim 1, wherein the alkali metal loaded alumina carrier in step (C) is thermally treated at 200° to 400° C. for 1 to 5 hours under vacuum.

11. The method of claim 1, wherein the alkylation of the side chain of the alkyl-substituted aromatic hydrocarbon in step (D) is conducted at 100° to 400° C. for 1 to 20 hours.

12. The method of claim 11, wherein the alkylation of the side chain of the alkyl-substituted aromatic hydrocarbon in step (D) is conducted at 150° to 300° C. for 2 to 10 hours.

* * * * *